United States Patent
Kitayama

(10) Patent No.: US 7,874,667 B2
(45) Date of Patent: Jan. 25, 2011

(54) EYEMASK

(75) Inventor: Hidehiro Kitayama, Tokyo (JP)

(73) Assignee: Nawari Trading Co., Ltd., Tokyo (JP)

( * ) Notice: Subject to any disclaimer, the term of this patent is extended or adjusted under 35 U.S.C. 154(b) by 0 days.

(21) Appl. No.: 12/387,139

(22) Filed: Apr. 28, 2009

(65) Prior Publication Data

US 2009/0316106 A1    Dec. 24, 2009

(30) Foreign Application Priority Data

Jun. 18, 2008    (JP)    .............................. 2008-183188

(51) Int. Cl.
G02C 7/16    (2006.01)
A61F 9/04    (2006.01)

(52) U.S. Cl. .................. 351/45; 351/46; 2/15

(58) Field of Classification Search ............. 351/45, 351/46, 132, 116, 111, 153, 41; 16/282; 128/858; 2/9, 12, 15, 440
See application file for complete search history.

(56) References Cited

U.S. PATENT DOCUMENTS

| | | | | | |
|---|---|---|---|---|---|
| 2,169,075 | A | * | 8/1939 | Shyer | ............................... 2/12 |
| 3,876,294 | A | * | 4/1975 | Kanbar et al. | .................. 351/46 |
| 4,452,516 | A | * | 6/1984 | Salia-Munoz | ................ 351/45 |
| 5,416,923 | A | * | 5/1995 | Peugh | ................. 2/9 |
| 5,673,432 | A | * | 10/1997 | Kitayama | ......................... 2/15 |
| 7,475,980 | B2 | * | 1/2009 | Tanir et al. | .................... 351/41 |
| 2006/0139568 | A1 | | 6/2006 | Kitayama | |

* cited by examiner

*Primary Examiner*—Hung X Dang
(74) *Attorney, Agent, or Firm*—Bucknam and Archer

(57) ABSTRACT

To attain the object of the invention to provide an eye mask of a simple structure that is easy to assemble using the integrally formed arc-shaped mask body, with the centrally located concave part abutting the nose of the wearer, the eye mask of the invention comprises an arc-shaped oblong mask body (1) integrally formed of resin, a concave (4) formed at the center of the mask body (1), a first and a second eye spot (5 and 6) comprising small perforated holes (2) formed on both sides of the concave (4) and temples (10) each mounted on both sides of the mask body (1) via a hinge (9), wherein the cross section of the mask body (1) perpendicular to its length direction has a C-curved surface.

4 Claims, 3 Drawing Sheets

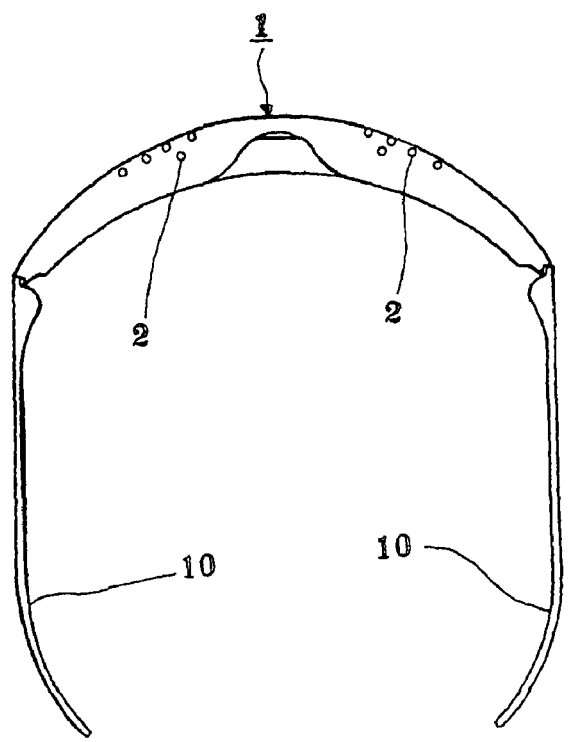
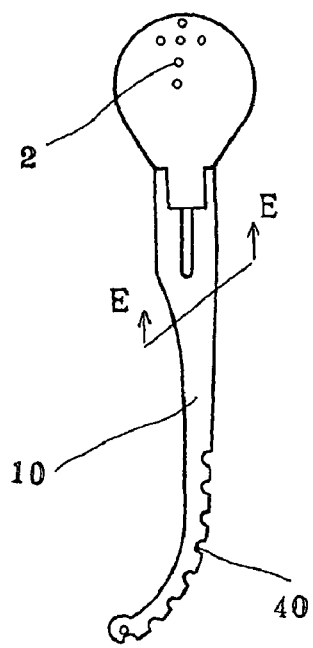
FIG. 6
FIG. 7
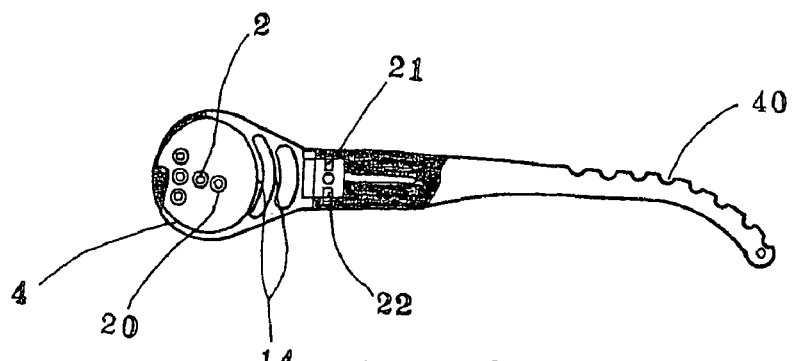
FIG. 8
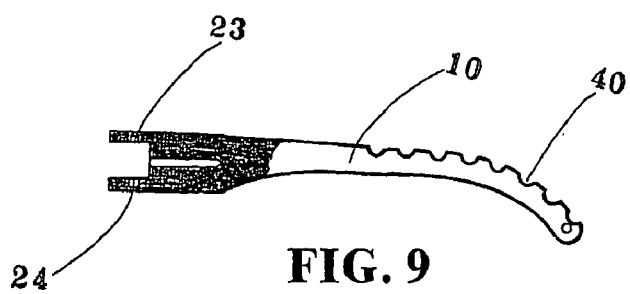
FIG. 9

EYEMASK

CROSS REFERENCE TO RELATED APPLICATIONS

Applicant claims priority under 35 U.S.C. §119 of Japanese Application No. JP2008-183188 filed Jun. 18, 2008.

FIELD OF THE INVENTION

The present invention relates to an improvement of eye mask for simpler structure and easier assembly by employing an integrally formed arc-shaped oblong mask body with a C-curved cross section.

BACKGROUND OF THE INVENTION

This type of eye mask conventionally uses a sheet-like mask body made of flat soft materials such as the first embodiment as disclosed in Document 1. The entire eye mask is large in size.

In the second embodiment, only the eye spots have a cupped shape and are connected to each other, with a temple attached to each eye spot.

Document 1: Japanese Laid-open Patent Application No. 2004-8736

Document 2: Japanese Laid-open Utility Model Application No. 1992-60223

SUMMARY OF THE INVENTION

Problems to Be Solved

Conventional eye masks as structured above have the following problems.

In the first conventional embodiment cited above, the entire product is basically a sheet so that a large area of the face is covered. Production cost is high because many parts are used. It is difficult to shield light for the mask is a sheet-like product.

In the second conventional embodiment cited above, two separate cup-like eye spots are used, requiring the assembly of a number of parts including connectors.

Both of the conventional embodiments cited above need a better fit to the face, and are not suitable for use for a long time.

Means to solve the Problems

The eye mask of the present invention comprises an arc-shaped oblong mask body integrally formed of resin, a concave formed on the mask body at the center of its length direction, a first and a second eye spot comprising small perforated holes located on both sides of the concave and a pair of temples each rotatably mounted on both sides of the mask body via a hinge, wherein the cross section of the mask body perpendicular to its length direction has a C-curved form. With the eye mask of the present invention, a circular frame is formed on the back of the mask body and the concave (4) serves as a nose bridge (12) at the lower section of the circular frame; a light shield is mounted on the concave; one or more inwardly projecting light shielding pieces are formed the inner wall of the mask body on both sides of the circular frame; said small holes are funnels with a tapered cross section; the cross section of the C-curved form is the thinnest at its center, with the thickness gradually increasing on both sides from the center; and the hinge comprises the first and the second posts formed on the end sections, and the first and the second holes engageably formed on the ends of temples with the first and the second posts, said posts having a mutually different diameter, and said holes a mutually different hole diameter

EFFECTS OF THE INVENTION

The present invention offers the following effects because of the unique structure detailed above.

As described in Claims 1, the entire eye area of the wearer is easily covered with a mask of a small area. For various types of faces, the eye mask of the present invention curves naturally according to the shape of the face. The inside of the mask is concave with a certain depth to allow the wearer to blink naturally. A good fit to the face is achieved because the eye mask of the present invention follows the shape of the face naturally. To maximize the pinhole effects (view function), the eye mask of the present invention is designed to derive darkroom effects effectively.

The eye mask of the present invention features an ergonomic structure and functions to remove physical and mental uneasiness and achieve mental stability. The product is generally designed to eliminate wastes and reduce the weight. It furthermore features the view function (pinholes), is compact in size, and allows use for many hours.

Mental stability is obtained and there is no sense of fatigue even when using for many hours. The eye mask of the present invention is easy to use and comfortable because it fits the face snugly. To maximize the pinhole effects, the light shield is carefully designed to prevent leakage of light from inside, assuring the maximum darkroom effect.

The eye mask of the present invention is integrally molded to make it lighter than conventional eye mask. For this reason, the product is more economical and comfortable to use. The present invention makes it possible to produce excellent eye masks that can be used safely and reliably.

Due to the structure as described in Claims 2 to 4, a nose bridge is provided in the middle of the circular frame to prevent the mask from slipping off the nose. A structure is obtained in which a certain area is required to enhance the light shielding effect so that the leakage of light from the nose bridge is prevented.

To enhance the darkroom effects, light shields are provided on the right- and left-hand sides of the mask body so that light will not leak from these areas.

Due to the structure of the eye mask as described in Claims 5 and 6, it is essential from the viewpoint of optics to make the upper part of the inner wall of the circular frame as thin as possible. Toward this end, the small holes on the inner wall are formed in the shape of a funnel to make the area around the small holes as thin as possible. Due to this design, all small holes look like a true circle relative to the rectilinear direction of light.

Due to the structure of the eye mask as described in Claims 7, connecting parts are aligned in a certain given direction, making it possible to prevent errors when assembling the right- and left-hand temples. The merits of this design include uniform workability and products, easier assembly, no need of skilled worker, and the reduction of the production cost.

BEST MODE FOR CARRYING OUT THE INVENTION

It is the object of the present invention to provide an eye mask of simple structure that is easy to assemble using the integrally formed arc-shaped oblong mask body with a C-curved cross-section.

BRIEF DESCRIPTION OF THE DRAWINGS

FIG. 6 is a plan view of FIG. 1;

FIG. 7 is a right side view of FIG. 6;

FIG. 8 is a cross-sectional view along section E-E of FIG. 7;

FIG. 9 is a cross-sectional view of the temple shown in FIG. 7;

DETAILED DESCRIPTION OF THE PREFERRED EMBODIMENTS

Embodiments

Figure 1:
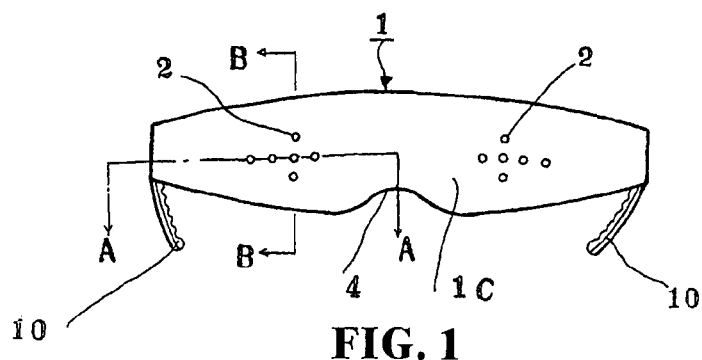
FIG. 1 is a front view of the eye mask of the present invention.
Figure 2:
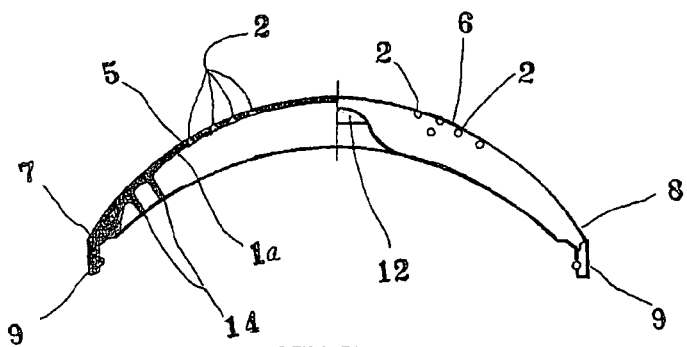
FIG. 2 is a cross-sectional view along section A-A of FIG. 1.
Figure 3:
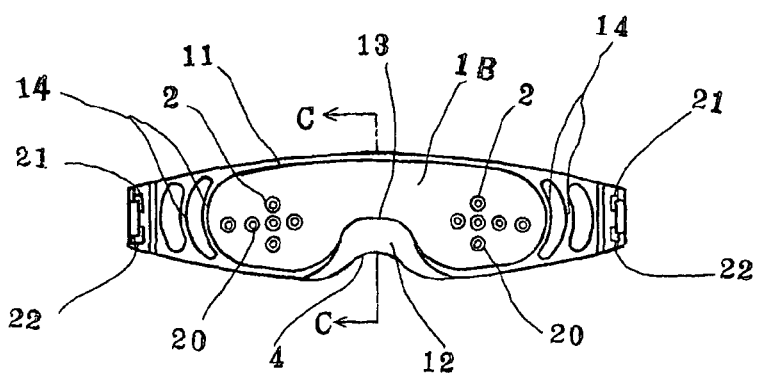
FIG. 3 is a rear view of FIG. 1.

Preferred embodiments of the eye mask of the present invention are described referring to the drawings. The item designated with reference number 1 in FIGS. 1 to 3 is the integrally resin made oblong mask body bent to an arc form. A concave 4 for contact against the nose is formed on the mask body 1 at the center of its length direction. The first and the second eye spots 5 and 6 comprising small perforated holes 2 are formed on both sides of the concave 4. A pair of temples 9 is movably connected via hinge 9 to the first and the second end sections 7 and 8 at the ends of the mask body 1.

Figure 4:
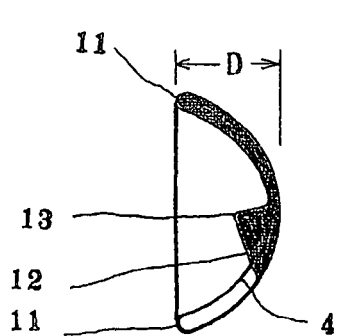
FIG. 4 is a cross-sectional view along section C-C of FIG. 3.
Figure 5:
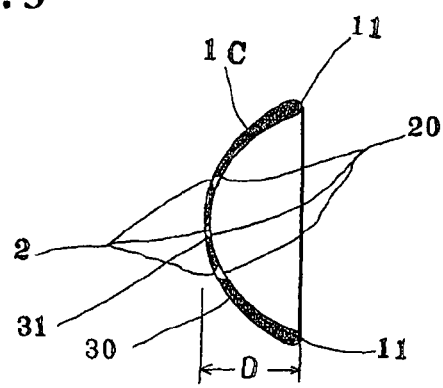
FIG. 5 is a cross-sectional view of FIG. 3.
Figure 10:
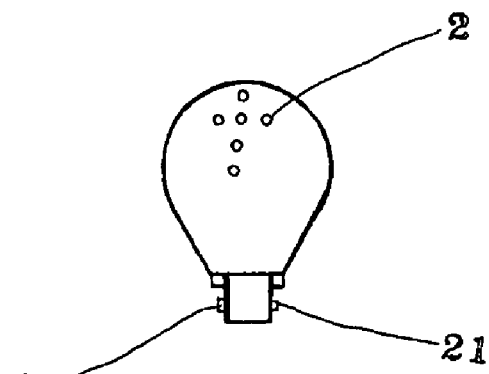
FIG. 10 is a side view of the critical parts of FIG. 7.
Figure 11:
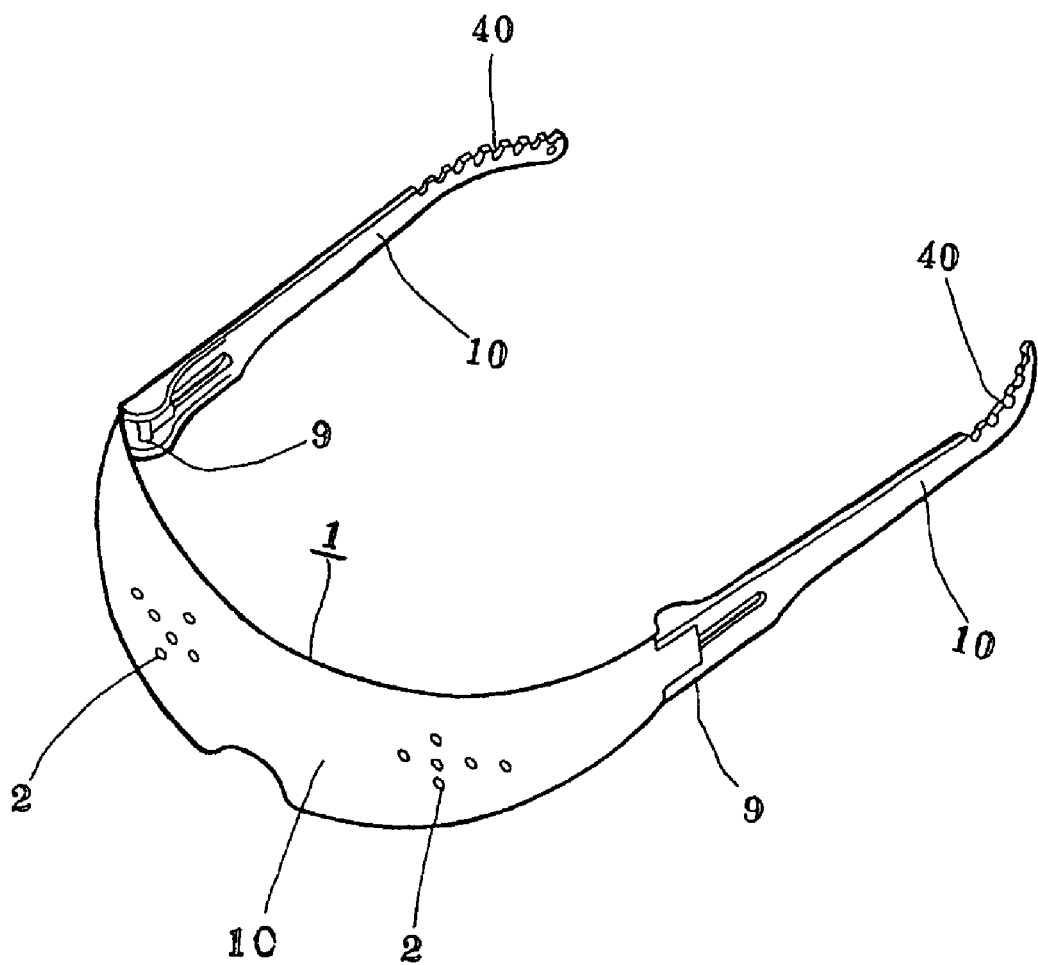
FIG. 11 is an oblique perspective view of FIG. 6.

The cross section of the mask body 1 perpendicular to its length direction has a C-curved form 30 with a depth D as shown in FIGS. 4 and 5. The inside is finished to a concave surface 1B while the outside surface is processed as a convex surface 1C.

A circular frame 11 is formed on the back of the mask body 1. The concave 4 is located at one portion of the lower part of the circular frame 11. The concave 4 forms the nose bridge 12. The upper part of the nose bridge 12 forms the installed light shield 13.

The light shield 13 is so structured that, when the nose contacts against the concave 4 of the mask body 1, external light will not enter the back side of the mask body 1.

One or more inwardly projecting light shielding pieces 14 are formed on both sides of the inner wall 1a on the mask body 1. The tips of the light shielding pieces 14 contact against the face snugly to prevent external light from entering the eye spots 5 and 6.

Small holes 2 on the eye spots have the form of a funnel 20, or are tapered, as shown in FIG. 5. The holes run through the mask body 1 from back to surface, with a diminishing diameter.

The first and the second posts 21 and 22 with mutually different diameter for forming the hinges 9 are formed on the end sections 7 and 8 of the mask body 1. The first and the second holes 23 and 24 with mutually different diameter for the temples are formed on the first and the second posts 21 and 22. The hinge 9 becomes operable when the first and the second posts 21 and 22 rotatably fit into the first and the second holes 23 and 24.

The cross section of the C-curved form of the mask body is the thinnest at its center 31, with the thickness gradually increasing toward the upper and lower edge on both sides from the center 31.

The center 31 provided with small holes 2 is very thin. For this reason, when the mask body 1 is worn, the walls of the small holes 2 are hardly visible because of the funnel-like shape of the small holes. The wearer of the eye mask therefore views as a true circle. It is possible to prevent viewing as anything other than true circles generated by the rectilinear direction of light. For this reason, the external view through the small holes 2 can be viewed through true circles when using the mask body 1.

The first and the second posts 21 and 22 for the hinge 9 have a mutually different diameter and he first and the second holes 23 and 24 have a mutually different diameter. When connecting the temples 10 to the mask body 1, therefore, the assembly work can be performed very easily without the possibility of mistaking the direction of connection. Each of the temples 10 is provided with grooves 40. A stopper (not shown) is selectively mounted on one of the grooves. By moving the stopper as required according to the size of the face and the ears, the wearer can freely adjust the fitness of the mask body 1 of the eye mask for the face.

A BRIEF DESCRIPTION OF REFERENCE NUMBER

1 Mask body
2 Small hole
1a Inner wall
4 Concave
1B Concave surface
1C Convex surface
10 Temple
5 First eye spot
6 Second eye spot
7 First end section
8 Second end section
9 Hinge
11 Circular frame
12 Nose bridge
13 Light shield
14 Light shielding piece
20 Funnel
21 First post
22 Second post
30 C-curved form
31 Center
40 Groove
23 First hole
24 Second hole

The invention claimed is:

1. An eye mask comprising an arc-shaped oblong mask body (1) integrally formed of resin, a concave (4) formed on the mask body (1) at a center in a length direction of the mask body (1), a first and a second eye spot (5 and 6) comprising small perforated holes (2) located on both sides of the concave (4) and temples (10) rotatably mounted on both end sections (7 and 8) of the mask body (1) via a hinge (9), wherein a cross section of the mask body perpendicular to the length direction of the mask body has a C-curved form (30), a circular frame (11) is formed on a rear side of the mask body (1), and the concave (4) serves as a nose bridge (12) at a lower part of the circular frame (11), a plurality of light shielding pieces (14) projecting to a height flush with the circular frame

(11) are formed on an inner wall (1a) of the mask body (1), on both sides of the circular frame (11).

2. The eye mask as claimed in claim 1 wherein a cross section of the C-curved form (30) is thinnest at its center (31), with a thickness gradually increasing toward an upper and a lower edges on both sides from the center (31), and the perforated holes (2), which are funnels (20) extending from the rear side to a front side of the mask body (1) and having a tapered cross section, are arranged in the center (31) where the thickness is least.

3. The eye mask as claimed in claim 2 wherein the hinge (9) comprises: a first post (21) and a second post (22) which are formed on each of the end sections (7 and 8); and a first hole (23) and a second hole (24) formed on one end of each temple (10) and engaged with the first post (21) and the second post (22), said posts (21 and 22) having a mutually different diameter and said holes (23 and 24) a mutually different diameter.

4. The eye mask as claimed in claim 1 wherein the hinge (9) comprises a first post (21) and a second post which are formed on each of the end sections (7 and 8) and a first hole (23) and a second hole (24) formed on one end of each temple (10) and engaged with the first post (21) and the second post (22), said first and second posts (21 and 22) having a mutually different diameter and said first and second holes (23 and 24) a mutually different diameter.

* * * * *